(12) United States Patent
Grichnik et al.

(10) Patent No.: US 7,805,421 B2
(45) Date of Patent: Sep. 28, 2010

(54) METHOD AND SYSTEM FOR REDUCING A DATA SET

(75) Inventors: Anthony J. Grichnik, Peoria, IL (US);
Michael Lee Taylor, Morton, IL (US);
Christos Nikolopoulos, Peoria, IL (US);
James Robert Mason, Peoria, IL (US);
Meredith Jaye Cler, Peoria, IL (US);
Gabriel Carl Hart, North Pekin, IL (US)

(73) Assignee: Caterpillar Inc, Peoria, IL (US)

( * ) Notice: Subject to any disclaimer, the term of this patent is extended or adjusted under 35 U.S.C. 154(b) by 395 days.

(21) Appl. No.: 11/979,409

(22) Filed: Nov. 2, 2007

(65) Prior Publication Data

US 2009/0119323 A1 May 7, 2009

(51) Int. Cl.
*G06F 7/00* (2006.01)
*G06F 17/00* (2006.01)

(52) U.S. Cl. ............... 707/696; 707/802; 707/E17.002; 705/2

(58) Field of Classification Search .......... 707/101, 707/696, 802, E17.002; 705/2, 3
See application file for complete search history.

(56) References Cited

U.S. PATENT DOCUMENTS

| | | | |
|---|---|---|---|
| 6,665,385 B2 * | 12/2003 | Rogers et al. .......... 379/106.02 |
| 6,915,254 B1 | 7/2005 | Heinze et al. | |
| 7,016,856 B1 | 3/2006 | Wiggins | |
| 7,069,227 B1 | 6/2006 | Lintel, III et al. | |
| 7,127,094 B1 * | 10/2006 | Elbaum et al. .............. 382/128 |
| 7,251,540 B2 | 7/2007 | Clarke et al. | |
| 7,487,134 B2 | 2/2009 | Grichnik et al. | |
| 7,689,383 B2 * | 3/2010 | Black et al. ................. 702/183 |
| 2001/0039503 A1 | 11/2001 | Chan et al. | |
| 2002/0143575 A1 * | 10/2002 | Hansen et al. ................. 705/2 |
| 2003/0046110 A1 | 3/2003 | Gagolak | |
| 2003/0061072 A1 | 3/2003 | Baker et al. | |
| 2003/0065535 A1 | 4/2003 | Karlov et al. | |
| 2003/0088363 A1 * | 5/2003 | Aronow ....................... 702/19 |
| 2005/0158767 A1 | 7/2005 | Haskell et al. | |
| 2005/0203828 A1 * | 9/2005 | Lyakovetsky ................ 705/38 |
| 2005/0251025 A1 * | 11/2005 | Hancu et al. ................ 600/420 |
| 2006/0084847 A1 | 4/2006 | Reed et al. | |
| 2006/0161459 A9 | 7/2006 | Rosenfeld et al. | |
| 2006/0229854 A1 | 10/2006 | Grichnik et al. | |
| 2006/0265253 A1 | 11/2006 | Rao et al. | |
| 2007/0106536 A1 | 5/2007 | Moore | |
| 2007/0156451 A1 * | 7/2007 | Gering .......................... 705/2 |
| 2007/0214013 A1 | 9/2007 | Silverman | |
| 2009/0024367 A1 | 1/2009 | Grichnik et al. | |
| 2009/0047694 A1 * | 2/2009 | Shuber ......................... 435/15 |
| 2009/0112533 A1 | 4/2009 | Grichnik et al. | |

* cited by examiner

*Primary Examiner*—Jean B. Fleurantin
*Assistant Examiner*—Phong Nguyen
(74) *Attorney, Agent, or Firm*—Finnegan, Henderson, Farabow, Garrett & Dunner LLC

(57) ABSTRACT

System and methods are provided for applying a dimensionality reduction process to a data set. The method includes obtaining a data set including a first set of variables and identifying collections of the first set of variables for replacement by a second set of variables. The method also includes replacing the collections of the first set of variables with the second set of variables and eliminating the first set of variables from the data set.

13 Claims, 2 Drawing Sheets

METHOD AND SYSTEM FOR REDUCING A DATA SET

TECHNICAL FIELD

This disclosure relates generally to data processing, and, more particularly, to methods and systems for reducing a data set.

BACKGROUND

Increasing amounts of memory for a computer have placed larger demands on computer processing. One field in which large amounts of data must be processed is health monitoring and diagnosis. Individuals, companies, and insurance companies desire to collect and analyze health data for as many individuals as possible to identify possible health risks and trends. For example, a company may collect and analyze health data for thousands of employees, each with diagnostic data related to dozens of diseases, prescribed medications, and health indicators (e.g., blood pressure, age, weight). The data can be stored in relational databases with the corresponding medical diagnostic codes. As the amount of health data increases, the ability to rapidly analyze it has suffered.

One tool that has been developed for managing a health and wellness program U.S. Patent Application Publication No. 2001/0039503 ("the '503 publication"). The '503 publication discloses collecting patient data from a variety of sources and filtering the patient data to discard some of the inputs that are not related to a particular illness that is being analyzed. The '503 publication analyzes the filtered data to provide recommendations to individuals based on identified health risks.

Although the tool of the '503 publication filters data that is unrelated to an analyzed illness, eliminating data can result in inaccurate predictions. For example, if the data is being analyzed for multiple diseases, eliminating data that is unrelated to a first disease may cause the '503 publication to improperly diagnose the patient for the second disease. Instead, summarizing, not eliminating, data would preserve data for diagnosis of multiple diseases. Moreover, where diagnosis of a particular disease involves analyzing hundreds of data points, the '503 publication fails to provide a method to reduce the data points in a manner that allows rapid processing without loss of accuracy.

The present disclosure is directed to overcoming one or more of the problems set forth above.

SUMMARY

In accordance with one aspect, the present disclosure is directed toward a computer-readable medium comprising instructions which, when executed by a processor, perform a method for applying a dimensionality reduction process to a data set. The method may include obtaining a data set including a first set of variables and identifying collections of the first set of variables for replacement by a second set of variables. The method may also include replacing the collections of the first set of variables with the second set of variables and eliminating the first set of variables from the data set.

According to another aspect, the present disclosure is directed toward a method for applying a dimensionality reduction process to a data set. The method may include obtaining a data set including a first set of variables and identifying collections of the first set of variables for replacement by a second set of variables. The method may also include replacing the collections of the first set of variables with the second set of variables and eliminating the first set of variables from the data set.

According to another aspect, the present disclosure is directed to a computer system including memory, at least one input device, and a central processing unit in communication with the memory and the at least one input device. The central processing unit may execute a method for applying a dimensionality reduction process to a data set. The method may include obtaining a data set including a first set of variables and identifying collections of the first set of variables for replacement by a second set of variables. The method may also include replacing the collections of the first set of variables with the second set of variables and eliminating the first set of variables from the data set.

DETAILED DESCRIPTION

Reference will now be made in detail to exemplary embodiments, which are illustrated in the accompanying drawings. Wherever possible, the same reference numbers will be used throughout the drawings to refer to the same or like parts.

Figure 1:
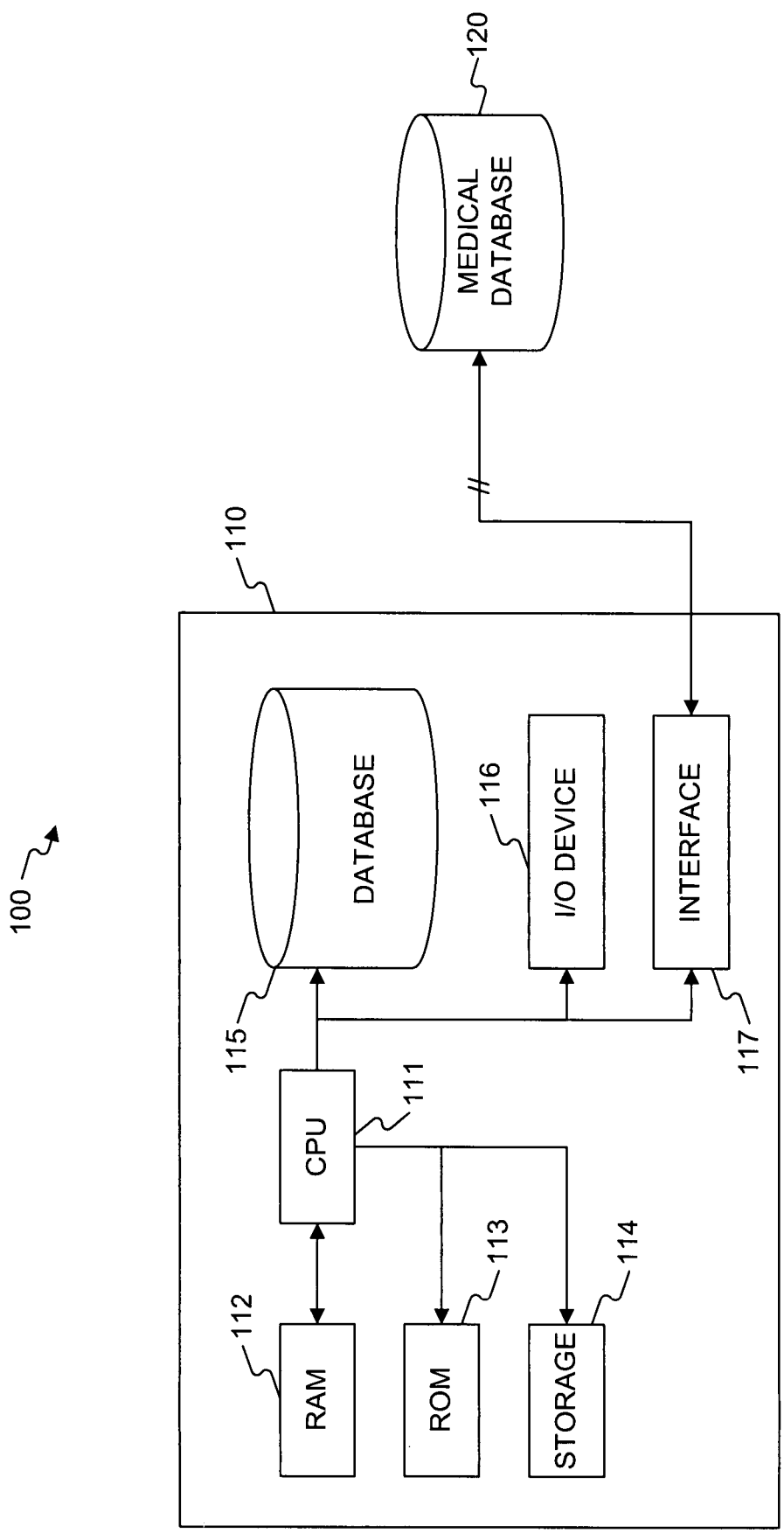
FIG. 1 is a block illustration of an exemplary disclosed system for reducing a data set.

FIG. 1 provides a block diagram illustrating an exemplary environment 100 for reducing a data set. Environment 100 may include a system 110 and a medical database 120. System 110 may be, for example, a general purpose personal computer or a server. Although illustrated as a single system 110, a plurality of systems 110 may connect to other systems, to a centralized server, or to a plurality of distributed servers using, for example, wired or wireless communication.

System 110 may include any type of processor-based system on which processes and methods consistent with the disclosed embodiments may be implemented. For example, as illustrated in FIG. 1, system 110 may include one or more hardware and/or software components configured to execute software programs. System 110 may include one or more hardware components such as a central processing unit (CPU) 111, a random access memory (RAM) module 112, a read-only memory (ROM) module 113, a storage 114, a database 115, one or more input/output (I/O) devices 116, and an interface 117. System 110 may include one or more software components such as a computer-readable medium including computer-executable instructions for performing methods consistent with certain disclosed embodiments. One or more of the hardware components listed above may be implemented using software. For example, storage 114 may include a software partition associated with one or more other hardware components of system 110. System 110 may include additional, fewer, and/or different components than those listed above, as the components listed above are exemplary only and not intended to be limiting.

CPU 111 may include one or more processors, each configured to execute instructions and process data to perform one or more functions associated with system 110. As illustrated in FIG. 1, CPU 111 may be communicatively coupled to RAM 112, ROM 113, storage 114, database 115, I/O devices 116, and interface 117. CPU 111 may execute sequences of computer program instructions to perform various processes, which will be described in detail below. The computer program instructions may be loaded into RAM for execution by CPU 111.

RAM 112 and ROM 113 may each include one or more devices for storing information associated with an operation of system 110 and CPU 111. RAM 112 may include a memory device for storing data associated with one or more operations of CPU 111. For example, ROM 113 may load instructions into RAM 112 for execution by CPU 111. ROM 113 may include a memory device configured to access and store information associated with system 110, including information for identifying a health risk and reducing diagnostic health data.

Storage 114 may include any type of mass storage device configured to store information that CPU 111 may need to perform processes consistent with the disclosed embodiments. For example, storage 114 may include one or more magnetic and/or optical disk devices, such as hard drives, CD-ROMs, DVD-ROMs, or any other type of mass media device.

Database 115 may include one or more software and/or hardware components that cooperate to store, organize, sort, filter, and/or arrange data used by system 110 and CPU 111. Database 115 may store data collected by system 110, such as diagnostic health data, as described in more detail below.

I/O device 116 may include one or more components configured to communicate information to a user associated with system 110. For example, I/O devices may include a console with an integrated keyboard and mouse to allow a user to input parameters associated with system 110. I/O device 116 may also include a display, such as a monitor, including a graphical user interface (GUI) for outputting information. I/O devices 116 may also include peripheral devices such as, for example, a printer for printing information and reports associated with system 110, a user-accessible disk drive (e.g., a USB port, a floppy, CD-ROM, or DVD-ROM drive, etc.) to allow a user to input data stored on a portable media device, a microphone, a speaker system, or any other suitable type of interface device.

The results of received data may be provided as an output from system 110 to I/O device 116 for printed display, viewing, and/or further communication to other system devices. Output from system 110 may also be provided to database 115 and to medical database 120.

Interface 117 may include one or more components configured to transmit and receive data via a communication network, such as the Internet, a local area network, a workstation peer-to-peer network, a direct link network, a wireless network, or any other suitable communication platform. In this manner, system 110 may communicate with other network devices, such as dictionary database 120, through the use of a network architecture (not shown). In such an embodiment, the network architecture may include, alone or in any suitable combination, a telephone-based network (such as a PBX or POTS), a local area network (LAN), a wide area network (WAN), a dedicated intranet, and/or the Internet. Further, the network architecture may include any suitable combination of wired and/or wireless components and systems. For example, interface 117 may include one or more modulators, demodulators, multiplexers, demultiplexers, network communication devices, wireless devices, antennas, modems, and any other type of device configured to enable data communication via a communication network.

Medical database 120 may store variables regarding individuals that may be useful in identifying potential health risks. The variables may be classified into one or more groups, such as continuous variables that can take on any value (e.g., blood pressure), ordinal variables identifying categories with an implied order (e.g., low, medium, high), categorical variables that are mutually exclusive (e.g., apple, orange, banana), and Boolean variables that indicate true or false (e.g., male or female). Exemplary variables include individual's height, weight, blood pressure, resting pulse, x-ray results, lab test results, health history, name, ethnicity, contact information (e.g., mailing address, e-mail address, phone numbers), the individual's insurance company and doctors, and any other information that may be useful for predicting a health risk. The health data may include a plurality of health care claim codes, such as International Statistical Classification of Diseases and Related Health Problems (ICD codes) that classify and identify diseases and related health problems; Current Procedural Terminology codes (CPT codes) that describe medical, surgical, and diagnostic services; and Generic Product Identifier codes (GPI codes) that identify drugs. Although several examples of health information have been provided, many other types of health information may be stored in medical database 120 as needed to identify a variety of diseases.

Although not illustrated, one or more servers may contain medical database 120. A server may collect data from a plurality of systems 110 to provide a central repository for health data. Moreover, medical database 120 may include one or more databases that are in the same or different location. Examples of reducing a data set by applying a dimensionality reduction process will be described below with reference to FIG. 2.

Those skilled in the art will appreciate that all or part of systems and methods consistent with the present disclosure may be stored on or read from other computer-readable media. Environment 100 may include a computer-readable medium having stored thereon machine executable instructions for performing, among other things, the methods disclosed herein. Exemplary computer readable media may include secondary storage devices, like hard disks, floppy disks, and CD-ROM; or other forms of computer-readable memory, such as read-only memory (ROM) 113 or random-access memory (RAM) 112. Such computer-readable media may be embodied by one or more components of environment 100, such as CPU 111, storage 113, database 115, medical database 120.

Furthermore, one skilled in the art will also realize that the processes illustrated in this description may be implemented in a variety of ways and include other modules, programs, applications, scripts, processes, threads, or code sections that may all functionally interrelate with each other to provide the functionality described above for each module, script, and daemon. For example, these programs modules may be implemented using commercially available software tools, using custom object-oriented code written in the C++ programming language, using applets written in the Java programming language, or may be implemented with discrete electrical components or as one or more hardwired application specific integrated circuits (ASIC) that are custom designed for this purpose.

The described implementation may include a particular network configuration, but embodiments of the present disclosure may be implemented in a variety of data communication network environments using software, hardware, or a combination of hardware and software to provide the processing functions.

Processes and methods consistent with the disclosed embodiments may reduce data sets. For example, system 110 may collect large amounts of health data from a plurality of individuals and summarize the health data into a smaller, reduced data set. As a result, system 110 may monitor and quickly identify health risks based on a smaller data set that ensures an accurate depiction of patient health data.

Exemplary processes and methods consistent with the claims will now be described with reference to FIG. 2.

INDUSTRIAL APPLICABILITY

The disclosed methods and systems provide a desired solution for reducing a data set. In one embodiment, a data set containing a plurality of medical codes may be reduced by analyzing the data set to identify groups of variables that may be replaced with a reduced set of equivalent variables. The reduced set of variables may be equivalent in the sense that they provide the same type of information needed to analyze the data, such as diagnosing a patient. Because the reduced data set may provide equivalent information, environment 100 may reduce the amount of data storage required, reduce the processing time for diagnosing patients, and maintain diagnostic precision.

Figure 2:
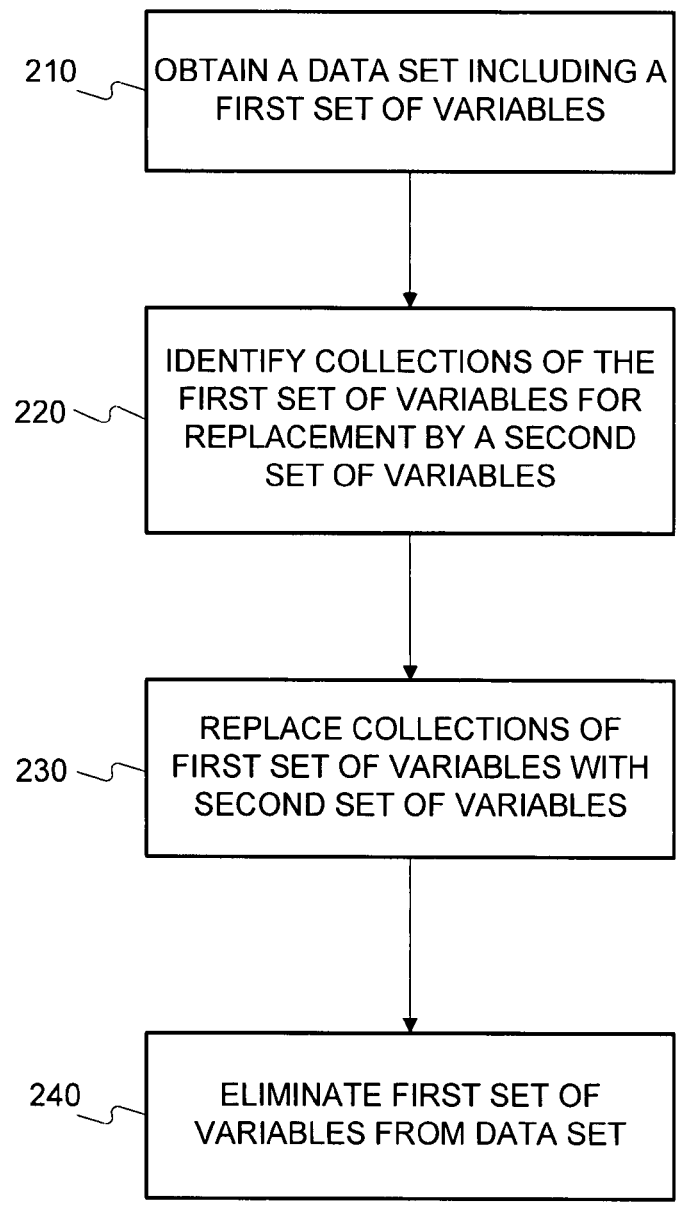
FIG. 2 is a flowchart illustration of an exemplary disclosed method for reducing a data set.

FIG. 2 is a flowchart illustration of an exemplary disclosed method 200 for reducing a data set. System 110 may perform method 200 periodically (e.g., every month), on demand, continuously, or at a triggering event, such as when an analysis of data is performed. System 110 may be run by, for example, a company or a health insurance company to reduce a data set related to, for example, health information. Doctors and medical students may also use method 200 to study changing health risks for a sample population. System 110 may use the reduced data set to predict the risk of any disease or any combination of diseases, such as various forms of cancer, heart disease, diabetes, cardiovascular disease, and other diseases.

Method 200 may begin with system 110 obtaining a data set including a first set of variables. The variables may relate to any type of information. For example, the variables may include health information for individuals (Step 210). System 110 may gather health information from, for example, doctors that individuals visit, insurance companies that individuals use, individuals through the use of one or more web-based forms, a company upon initial hiring of individuals (e.g., performing a physical or drug test), or any other source. System 110 may store the health information in, for example, database 115 and medical database 120. Individuals may also identify the amount of health information that system 110 can collect, allowing individuals to maintain their privacy.

Exemplary health data may include health data claim codes, such as International Statistical Classification of Diseases and Related Health Problems (ICD codes, such as ICD-9) that classify and identify diseases and related health problems; Current Procedural Terminology codes (CPT codes) that describe medical, surgical, and diagnostic services; and Generic Product Identifier codes (GPI codes) that identify drugs. These codes may each include a plurality of alphanumeric characters depending on the corresponding standard. Some of the characters may identify a category or type of disease or drug, while other characters may indicate a particular procedure or drug dose. For example, an ICD code for diabetes may begin with 250, with 250.0 indicating diabetes with no mention of complication, 250.1 indicating diabetes with ketoacidosis, 250.2 indicating diabetes with hyperosmolarity, and other codes from 250.3 through 250.9 indicating further permutations of diabetes. Using ICD codes for diabetes is only one example of medical codes; many other codes exist for diagnosing and treating diseases.

System 110 may obtain a table or access a database, such as medical database 120, including all of the possible medical codes for individuals included in the data set. For example, if a company has one thousand employees, each individual may have entries for each possible medical code. If the data set is a table, each employee may be listed in a row, with possible diseases and drugs identified in each column based on medical codes. Entries may include, for example, a Boolean indicator of whether the individual has been diagnosed for a claim code. If an individual has been diagnosed with a disease associated with a particular claim code more than once, or if the individual has been repeatedly prescribed a medication, the corresponding entries may repeat. Depending on the complexity and type of data, the first set of variables may include millions of entries in the data set obtained in Step 210.

Next, system 110 may identify collections of the first set of variables for replacement by a second set of variables (Step 220). The identification of variables for replacement may ensure that the data set will include all of the information necessary to perform the desired analysis. In the medical field, for example, system 110 may identify variables for replacement when diagnosis can be performed using a reduced data set. Several exemplary methods for identifying a first set of variables for replacement by a second set of variables will now be described.

One technique includes identifying a first set of variables that include multiple entries for the same event within a predetermined amount of time. For example, assume that an individual has taken a drug multiple times within a year. Variables may exist in the first data set for each date a patient took the drug, or each date an individual was prescribed the drug. That is, each date that a patient took or was prescribed a drug may include a separate variable in the data set. These variables correspond to the same event, prescribing or taking the drug, and may occur within a predetermined amount of time.

A second technique for identifying a first set of variables for replacement by a second set of variables includes a critical claims indicator. A critical claims indicator may represent a first set of variables that are related to each other and originated within a predetermined amount of time. For example, prescription of a drug may relate to prescription of one or more other drugs, such as when a patient is prescribed a plurality of drugs to treat a particular disease (e.g., cancer). If the prescriptions fall within a predetermined amount of time from each other, the prescriptions may be identified as a first set of related variables. As another example, assume an individual was tested for diabetes and the test for diabetes initiated under the 250.xx ICD code. If the first data set includes another 250.xx ICD code for the individual within a predetermined amount of time, both of the entries may be related. For example, if a patient is tested for a disease and then treated for the disease, multiple claim codes may exist with a common pattern (e.g., 250.xx for diabetes). System 110 may also relate claim codes belonging to different standards, such as correlating diagnostic claim codes with prescription drug claim codes, to formulate the critical claims indicator by using a frequency of occurrences to summarize each individual variable.

A third technique for identifying a first set of variables for replacement by a second set of variables includes hashing. As described above, claim codes may include related portions based on the identified disease, treatment, or drug. For example, all variables including the 250.xx IC9 code may relate to diabetes. Medical codes that share a common claim code or a portion of a common claim code may be reduced or combined into a more generic category using hashing, as described below.

Further, system 110 may replace collections of the first set of variables with the second set of variables (Step 230). Replacement may occur using any number of techniques designed to reduced the number of stored variables while maintaining enough information to accurately analyze the data.

For example, applying the first technique regarding a set of variables for the same event within a period of time, all of the related variables may be replaced with a single variable. Assume that an individual has taken a drug ten times in the last six months. Rather than storing individual entries for each time that the individual took the drug (the first set of variables), only the number of times that a user took the drug may be stored, in this example the continuous variable ten (the second set of variables). Accordingly, duplicative entries may be eliminated where multiple entries relate to the same event within a predetermined period of time.

Applying the second technique, a critical claims indicator, may replace collections of the related first set of variables occurring within a predetermined period of time with a second set of variables. For example, assume an individual's record indicates multiple ICD codes related to diabetes, such as diagnosis, treatment, and follow up care. Further assume the individual's record includes a plurality of drug prescriptions related to diabetes treatment. System 110 may replace these related entries with a single variable indicating the number of related variables occurring within a predetermined period of time, such as one year, or a variable simply indicating the individual has the related disease (e.g., diabetes). For example, if a user has a medical code for diabetes testing, two medical codes for diabetes treatment, and three medical codes for prescription of drugs for treating diabetes, the collection of these variables may be replaced with a critical claims indicator for diabetes equal to six (1+2+3).

System 110 may reduce the first set using a critical claim indicator if a given number of variables exist within a predetermined time to ensure accurate diagnosis. For example, if an individual has only two medical codes related to diabetes within a year, system 110 may identify that the patient likely does not have diabetes, and the first set of variables (both medical codes) should not be replaced. Instead, system 110 may eliminate the first set of variables related to diabetes because it is unlikely the individual has diabetes based on the few number of medical codes related to diabetes within the last year.

System 100 may also apply a third technique to replace a first set of variables with a second set of variables using hashing. System 110 may combine the code indicators for multiple diseases, treatments, and drug prescriptions into a combined string and search for one or more predetermined strings within the combined string. For example, assume an individual has an ICD9 code of ABCD, which indicates a test for diabetes; a treatment code of EFGH, which indicates treatment for diabetes; and prescription codes of IJKL, which indicates drugs for treating diabetes. System 110 may combined the codes into a single string—ABCDEFGHIJKL— and search the single string for known patterns. In this example, the combined string is a perfect match for an indicator of diabetes. The combined string may therefore be replaced with a condensed string, such as DB to indicate diabetes, and stored as the second set of variables. Medical codes may also be combined with other health data, such as an individual's sex, prior to performing the hash. System 110 may identify patterns for hashing based on experience and input from medical healthcare professionals.

System 110 may control the preciseness of a match that is required before replacing the first set of variables with the second set. As another example of hashing, a common set of variables for an individual may indicate that the individual has a defined height (5FT), weight (160LBS), gender (M), and vitamin prescription (AB). The combined string— 5FT160LBSMAB—may be reduced to a simplified variable, such as P1 to indicate pattern one. Moreover, system 110 may allow fuzzy hashing, such that combinations of strings that substantially match a defined pattern may be represented by a simplified variable. Continuing with the example above, assume an individual has a weight of 150 lbs instead of 160 lbs. The resulting combined string—5FT150LBSMAB— may still be represented by a simplified variable P1 because the pattern substantially matches. System 110 may determine the amount of fuzziness to allow based on input from medical professions regarding accurate diagnosis using health data. Although exemplary hashing algorithms have been described, many other hashing algorithms may be employed to reduce the first set of variables into a second set of variables.

Next, system 110 may eliminate the first of variables from the data set (Step 240). Using the first technique, system 110 may eliminate all of the variables for entries of the same event and replace the variables with a single frequency variable. Applying the second technique, system 110 may replace all of the variables related to a common disease, including diagnosis, treatment, and prescriptions, with a numerical critical claim indicator that may identify whether an individual has a disease. If the numerical indicator is equal to or above a threshold, such as two occurrences in the last six months, the individual may be diagnosed with the disease, or system 110 may perform further testing of the individual. If, however, the numerical indicator is below a threshold, the individual may be diagnosed as not having the disease, and system 110 may discard the related entries. In the third technique, the first set of variables may be eliminated by replacing the variables with a single, condensed string, as described above.

Variables may be eliminated or discarded, for example, at run-time while executing a model to diagnose a patient, in advance of executing a model, or when the first set of variables are initially stored by system 110. Moreover, system 110 may maintain a complete copy of the first set of variables to ensure that all of the available information will exist for future use. For example, medical database 120 may store a complete and persistent copy of all health data, whereas database 115 may store the reduced data set including the second set of variables, with the first set of variables having been eliminated.

Although not illustrated, environment 100 may use the reduced data set in one of a plurality of models to diagnose a patient. For example, a model as disclosed in U.S. Patent Application Publication No. 2006/0229854 by Grichnik et al. may be used to perform probabilistic modeling. Other models and techniques may be employed, depending on the amount and type of data, to perform a variety of analyses.

While environment 100 and method 200 have been described in the context of medical analysis and diagnosis, the disclosed systems and methods may be applied to any field desiring data reduction. For example, the critical claims indicator may be applied to an automobile diagnosis. In this example, the critical claims indicator may identify whether a threshold measured value, such as oil pressure, has exceeded a defined level within a period of time, such as one month or 1,000 miles of operation. Moreover, the disclosed hashing techniques may be applied to reduce any data set relying on codes with patterns. For example, automobile part numbers may share common digits, allowing all engine parts to be hashed into a reduced data set, all suspension parts to be hashed into a reduced data set, and so on. Further, the disclosed method for summarizing the number of times an event occurs, rather than storing individual logs for each event, may apply to a variety of contexts. One exemplary context may indicate that an operating system for a computer was rebooted three times within a week. Rather than storing the specific error codes for each time the computer was rebooted, only the number three may be stored, which reduces the amount of retained data and still allows identifying a solution, such as reinstalling the operating system. These contexts for applying the disclosed systems and methods are exemplary only and not intended to be limiting.

It will be apparent to those skilled in the art that various modifications and variations may be made to the disclosed methods. Other embodiments of the present disclosure will be apparent to those skilled in the art from consideration of the specification and practice of the present disclosure. It is intended that the specification and examples be considered as exemplary only, with a true scope of the present disclosure being indicated by the following claims and their equivalents.

What is claimed is:

1. A computer-implemented method for applying a dimensionality reduction process to a medical data set, comprising:
   obtaining a data set stored in a medical database, the data set including a set of medical data entries relating to medical events for individuals in a population;
   identifying a collection of the set of medical data entries relating to a common medical event for an individual in the population for replacement by a representative medical data entry for the common medical event, the identifying including identifying medical data entries of the set that are associated with medical events relating to the common medical event and occurring within a predetermined period of time; and
   reducing the size of the medical database by:
      replacing the identified collection of medical data entries with the representative medical data entry for the common medical event in the medical database, the representative medical data entry including a numerical indicator representing a number of the medical data entries in the identified collection; and
      eliminating the identified collection of medical data entries from the medical database.

2. The method of claim 1, wherein:
   the set of medical data entries includes medical codes and dates of occurrence of the events related to the medical data entries; and
   the medical events include at least one of a diagnosis of an individual and creating a prescription for an individual.

3. The method of claim 1, wherein:
   the identified collection of medical data entries represents a diagnosis of the individual for one or more diseases; and
   if a value of the numerical indicator is below a threshold, the individual is diagnosed as not having the disease.

4. The method of claim 1, wherein:
   the set of medical data entries includes medical codes; and
   replacing includes combining the medical codes associated with the identified collection of medical data entries into a string.

5. A computer-readable medium comprising instructions which, when executed by a processor, perform a method for applying a dimensionality reduction process to a medical data set, the method comprising:
   obtaining a data set stored in a medical database, the data set including a set of medical data entries relating to medical events for individuals in a population;
   identifying a collection of the set of medical data entries relating to a common medical event for an individual in the population for replacement by a single medical data entry representative of at least some of the medical data entries relating to the common event, the identifying including identifying medical data entries of the set that are associated with medical events relating to the common medical event and occurring within a predetermined period of time; and
   reducing the size of the medical database by:
      replacing the identified collection of medical data entries with the representative medical data entry for the common medical event in the medical database, the representative medical data entry including a numerical indicator representing a number of the identified collection of medical data entries; and
      eliminating the identified collection of medical data entries from the medical database.

6. The computer-readable medium of claim 5, wherein:
   the set of medical data entries includes medical codes and dates of occurrence of the events related to the medical data entries; and
   the medical events include at least one of a diagnosis of an individual and creating a prescription for an individual.

7. The computer-readable medium of claim 5, wherein:
   the identified collection of medical data entries represents a diagnosis of the individual for one or more diseases; and
   if a value of the numerical indicator is below a threshold, the individual is diagnosed as not having the disease.

8. The computer-readable medium of claim 5, wherein:
   the set of medical data entries includes medical codes; and
   replacing includes combining the medical codes associated with the identified collection of medical data entries into a string.

9. The computer-readable medium of claim 5, wherein the method further includes using the data set to diagnose a patient for one or more diseases.

10. A system for applying a dimensionality reduction process to a data set, the system comprising:
    a medical database storing a data set including medical data entries relating to medical events for individuals in a population;
    at least one input device; and
    a central processing unit in communication with the medical database and the at least one input device, wherein the central processing unit:
       obtains the data set from the medical database;
       identifies a collection of the set of medical data entries relating to a common medical event for an individual in the population for replacement by a representative medical data entry for the common medical event, the identifying including identifying medical data entries of the set that are associated with medical events relating to the common medical event and occurring within a predetermined period of time; and
       reduces the size of the medical database by:
          replacing the identified collection of medical data entries with the representative medical data entry for the common medical event in the medical database, the representative medical data entry including a numerical indicator representing a number of the identified collection of medical data entries; and
          deleting at least some of the identified collection of medical data entries from the medical database.

11. The system of claim 10, wherein:
    the set of medical data entries includes medical codes and dates of occurrence of the medical events related to the medical data entries; and the medical events include at least one of a diagnosis of an individual and creating a prescription for an individual.

12. The system of claim 10, wherein:

the identified collection of medical data entries represents a diagnosis of the individual for one or more diseases; and if a value of the numerical indicator is below a threshold, the central processing unit is configured to diagnose the individual as not having the disease, and to update the medical database based on the diagnosis.

13. The system of claim 10, wherein:

the set of medical data entries includes medical codes; and the central processing unit replaces the identified collection of medical data entries by combining the medical codes associated with the identified collection of medical data entries into a string.

* * * * *